United States Patent
Park et al.

(10) Patent No.: US 11,839,684 B2
(45) Date of Patent: Dec. 12, 2023

(54) MUCOADHESIVE PHARMACEUTICAL COMPOSITION AND PREPARATION METHOD THEREFOR

(71) Applicant: SAMYANG HOLDINGS CORPORATION, Seoul (KR)

(72) Inventors: Sang Yeob Park, Daejeon (KR); Jong Won Yoon, Daejeon (KR)

(73) Assignee: SAMYANG HOLDINGS CORPORATION, Seoul (KR)

(*) Notice: Subject to any disclaimer, the term of this patent is extended or adjusted under 35 U.S.C. 154(b) by 6 days.

(21) Appl. No.: 17/389,132

(22) Filed: Jul. 29, 2021

(65) Prior Publication Data

US 2021/0353530 A1     Nov. 18, 2021

Related U.S. Application Data

(62) Division of application No. 16/067,384, filed as application No. PCT/KR2016/015445 on Dec. 29, 2016, now abandoned.

(30) Foreign Application Priority Data

Dec. 30, 2015 (KR) .......................... 10-2015-0190402

(51) Int. Cl.
*A61K 9/00*     (2006.01)
*A61K 47/32*     (2006.01)
(Continued)

(52) U.S. Cl.
CPC ............ *A61K 9/006* (2013.01); *A61K 9/0065* (2013.01); *A61K 9/1635* (2013.01);
(Continued)

(58) Field of Classification Search
CPC .... A61K 9/006; A61K 9/0065; A61K 9/1635; A61K 9/1652; A61K 9/2059;
(Continued)

(56) References Cited

U.S. PATENT DOCUMENTS 4,501,835 A    2/1985   Berke
6,271,206 B1*   8/2001   Pillai ...................... C12N 15/88
                                             435/320.1

(Continued)

FOREIGN PATENT DOCUMENTS

CN     102552247 A  *   7/2012
CN     102010627 B     11/2012
(Continued)

OTHER PUBLICATIONS

Chitosan: https://www.sigmaaldrich.com/us/en/product/aldrich/419419 (Year: 2003).*

(Continued)

*Primary Examiner* — Hong Yu
(74) *Attorney, Agent, or Firm* — Birch, Stewart, Kolasch & Birch, LLP (57) ABSTRACT

Disclosed is a mucoadhesive pharmaceutical composition comprising a poly-ionic complex of chitosan and a polyacrylic acid polymer. As an oral formulation, the composition has the extended retention time in the gastrointestinal tract by its mucoadhesive and swelling properties, which is useful as sustained release formulations, retentive formulations of active ingredients with limited absorption regions, and active ingredients with pH dependent solubility.

5 Claims, 1 Drawing Sheet (51) Int. Cl.
*A61K 47/36* (2006.01)
*A61K 47/42* (2017.01)
*A61K 9/16* (2006.01)
*A61K 47/10* (2017.01)
*B82Y 5/00* (2011.01)

(52) U.S. Cl.
CPC ............ *A61K 9/1652* (2013.01); *A61K 47/10* (2013.01); *A61K 47/32* (2013.01); *A61K 47/36* (2013.01); *A61K 47/42* (2013.01); *B82Y 5/00* (2013.01)

(58) Field of Classification Search
CPC ........ A61K 47/32; A61K 47/36; A61K 47/42; A61K 47/10; B82Y 5/00
See application file for complete search history.

(56) References Cited

U.S. PATENT DOCUMENTS

| | | | |
|---|---|---|---|
| 9,078,805 B2* | 7/2015 | Mueller | A61J 3/00 |
| 2010/0330167 A1 | 12/2010 | Sung et al. | |
| 2012/0196873 A1 | 8/2012 | Nolte et al. | |
| 2012/0231069 A1 | 9/2012 | Nowotnik et al. | |
| 2013/0059000 A1 | 3/2013 | Wong et al. | |
| 2015/0104484 A1* | 4/2015 | Schlenoff | A61K 47/585 |
| | | | 514/11.3 |

FOREIGN PATENT DOCUMENTS

| | | | |
|---|---|---|---|
| WO | WO 03/068843 A1 | | 8/2003 |
| WO | WO 03/097714 A1 * | | 11/2003 |

OTHER PUBLICATIONS

Cho J et al.: Viscoelastic properties of chitosan solutions: Effect of concentration and ionic strength, https://www.sciencedirect.com/science/article/pii/S0260877405001901. (Year: 2005).*

Arora et al., "Formulation and Evaluation of Controlled Release Mucoadhesive Matrix Tablets: Assessment of Myrrh Oleo Gum Resin as a Natural Pharmaceutical Excipient". International Journal of Pharmaceutical Sciences and Drug Research, 2011, vol. 3, No. 2, pp. 84-88.

Chitosan: retrieved from internet: http://www.sigmaaldrich.com/catalog/product/aldrich/448869?lang=en&region=US. Retrieved on May 23, 2019.

Cho et al., "Preparation of Mucoadhesive Chitosan-Poly (Acrylic acid) Microspheres by Interpolymer Complexation and Solvent Evaporation Method II", Archives of Pharmacal Research, 2005, vol. 28, No. 5, pp. 612-618.

European Search Report dated Aug. 23, 2019 for EP 16882104.9.

Gujarathi et al., "pH sensitive polyelectrolyte complex of O-carboxymethyl chitosan and poly (acrylic acid) cross-linked with calcium for sustained delivery of acid susceptible drugs", International Journal of Pharmaceutics, 2012, vol. 436, pp. 418-425. See the entire document.

Hagesaether et al., "Mucoadhesion and drug permeability of free mixed films of pectin and chitosan: An in vitro and ex vivo study", European Journal of Pharmaceutics and Biopharmaceutics, 2009, vol. 71, pp. 325-331.

Hu et al., "Synthesis and characterization of chitosan-poly (acrylic acid) nanoparticles", Biomaterials, vol. 23, 2002, pp. 3193-3201.

International Search Report (PCT/ISA/210) issued in PCT/KR2016/015445, dated Mar. 27, 2017.

Ketjinda et al., "Development of Push-Pull Osmotic Tablets Using Chitosan-Poly(Acrylic Acid) Interpolymer Complex as an Osmopolymer", AAPS PharmSciTech, 2010, vol. 12, No. 1, pp. 132-140.

Saberi et al., "Chitosan-Poly Acrylic Acid Hybrid Nano Particle as a Novel Bioadhesive", Proceedings of 5th International Congress on Nanoscience & Nanotechnology. Tehran, Iran, 2014, pp. 1-3. See abstract: p. 1, right column; p. 2, right column; and p. 3. table 3. left column.

Sajeesh et al., "Mucoadhesive hydrogel microparticles based on poly (methacrylic acid-vinyl pyrrolidone)-chitosan for oral drug delivery", Drug Delivery, 2011, vol. 18, No. 4, pp. 227-235. See the entire document.

Sajeesh et al. "Novel pH responsive polymethacrylic acid-chitosan-polyethylene glycol nanoparticles for oral peptide delivery", Journal of Biomedical Materials Research Part B-Applied Biomaterials, 2006, vol. 76B, pp. 298-305. See abstract; and pp. 298, 299, 303.

Torrado et al., "Chitosan-poly(acrylic) acid polyionic complex: in vivo study to demonstrate prolonged gastric retention", Biomaterials, 2004, vol. 25, pp. 917-923. See abstract; and pp. 917, 918, 922.

Tuntikulwattana et al., "Fabrication of chitosan-polyacrylic acid complexes as polymeric osmogents for swellable micro/nanopourous osmotic pumps", Drug Development and Industrial Pharmacy, 2011, vol. 37, No. 8, pp. 926-933.

* cited by examiner

MUCOADHESIVE PHARMACEUTICAL COMPOSITION AND PREPARATION METHOD THEREFOR

CROSS-REFERENCE TO RELATED APPLICATIONS

This application is a Divisional of copending application Ser. No. 16/067,384, filed on Jun. 29, 2018, which is the National Phase under 35 U.S.C. § 371 of International Application No. PCT/KR2016/015445, filed on Dec. 29, 2016, which claims the benefit under 35 U.S.C. § 119(a) to Patent Application No. 10-2015-0190402, filed in Republic of Korea on Dec. 30, 2015, all of which are hereby expressly incorporated by reference into the present application.

TECHNICAL FIELD

The present disclosure relates to a mucoadhesive pharmaceutical composition, and more specifically, a mucoadhesive pharmaceutical composition or formulation which is applicable as a gastro-intestinal retentive formulation, a sustained release oral formulation, etc. for an active ingredient having limited absorption region, by increasing the retention time in gastro-intestinal tract due to mucoadhesiveness particularly in gastro-intestinal tract and swelling property.

BACKGROUND ART

Chitin, a natural polymer occurring in the second largest quantity next to cellulose among natural polymers in the natural system, is a natural polysaccharide having a molecular weight of about 1,000,000 or higher wherein N-acetyl-D-glucosamine is linked by β-1,4-linkage. It is contained in a large amount mainly in shells of crustaceans such as crab, shrimp, etc. Chitosan is a natural cationic polysaccharide obtained by deacetylation of N-acetyl group in chitin followed by substitution with amino group (—$NH_2$). Its formal name is poly-β-(1-4)-2-amino-2-deoxy-D-glucan. Chitosan is non-toxic and biodegradable, and has fat-binding ability remarkably stronger than conventional dietary fibers in foods. Thus, it reduces intestinal fat absorption and lowers cholesterol level in serum in animal test, thereby preventing and treating hypercholesteremia and arteriosclerosis. It also has various physiological activities such as protection of liver from alcoholic hepatic injury, antibiotic activity, moisturizing property and emulsion stability, various physiological functions of dietary fibers, anticancer effect, immune enhancing effect, antidiabetic effect, wound healing effect, antimicrobial effect, etc. In particular, it binds to the mucous layer of buccal, nasal and intestinal cavities, etc. thereby promoting absorption of an active ingredient. Thus, many studies have been conducted to apply it as an absorption enhancer in oral and other various formulations of proteinaceous active ingredients or poorly absorbable active ingredients. In addition, because it has a cationic property in an aqueous solution, it can form a complex with anionic genetic material. Thus, researches have been actively made to apply chitosan or its derivatives as gene delivery vehicle. Furthermore, chitosan has good mucoadhesiveness, which is known to mainly result from charge interaction, i.e. charge interaction between cations of chitosan and anions of gastro-intestinal surface. Chitosan is insoluble in water but dissolves well in an acidic condition. It becomes insoluble at a pH of about 6.0 or higher and in a basic solution. Therefore, when used in an oral formulation, it may be dissolved completely and disappear in an acidic condition such as gastric environment. In order to prevent this, a poly-ionic complex (PIC) with an anionic polymer has been considered.

Polyacrylic acid, which is a representative anionic polymer, is a homopolymer or a crosslinked polymer of acrylic acids. In the field of pharmaceuticals or cosmetics, it has been utilized for various uses such as thickener, dispersant, emulsifier, superabsorbent polymer, etc. Polyacrylic acid may be a linear polymer or in the form of crosslinked acrylic acids by using allyl ester of sucrose or pentaerythritol. Carbomer or Carbopol is a crosslinked polymer of acrylic acids. Due to its molecular characteristics, it forms a gel showing viscosity at a pH between 4 and 10, the viscosity of which decreases at a low pH of 3 or lower, or a high pH of 10 or higher.

A mucoadhesive formulation can be utilized as an oral formulation such as a sustained release formulation, a gastro-intestinal retentive formulation, etc., due to its good adhesiveness to mucous membranes. In addition, it can be utilized in ophthalmic formulations, vaginal or rectal formulations, ointments, etc.

U.S. Pat. No. 4,501,835 discloses a membrane formed from a poly-ionic complex of chitosan and polyacrylic acid. It discloses that the membrane can be prepared in an acidic aqueous solution and the molecular weight of polyacrylic acid must be 10,000 or lower so as to be manufactured into a film. It discloses its application as a separation membrane in the presence of an organic solvent. However, the poly-ionic complex has too low molecular weight as a drug carrier.

U.S. Pat. No. 8,454,966 discloses a vaccine carrier with improved cell permeability of nanoparticles prepared from chitosan and γ-glutamic acid. Chitosan is one of substances studied for application in various drug carriers.

Torrado et al. Biomaterials 25 (2004) 917-923 suggests hydrogel of poly-ionic complex of chitosan and polyacrylic acid for delivering amoxicillin. Polyacrylic acid and chitosan were used with the ratio of 1:2.5 to 1:15, and amoxicillin trihydrate was used as an active ingredient. The hydrogel was prepared by dissolving polyacrylic acid in an aqueous solution of acetic acid, adding amoxicillin thereto and mixing homogeneously, adding chitosan thereto and adjusting the pH, pouring the obtained mixture into a mold, and then, freeze-drying it. The obtained hydrogel was cut into a proper size for use in subsequent experiments.

Such prior arts neither teach nor suggest mucoadhesive drug carrier comprising a poly-ionic complex of chitosan and polyacrylic acid. In particular, since the poly-ionic complex was prepared in an acidic condition or at a relatively low pH, amine groups of chitosan were ionized to cations, but carboxyl groups of polyacrylic acid were scarcely or partially ionized to anions, thus forming incomplete poly-ionic complex. In addition, because it was not easy to find a solvent which can solubilize the formed poly-ionic complex, it has only a limited application, e.g. as a membrane formed through simple drying or freeze drying, etc. or as a hydrogel. In particular, studies on application as an oral drug carrier could hardly be progressed. In some cases, conventional facilities for manufacturing solid formulations were inapplicable for its production, but special facilities were required or only lab-scale production was available. Furthermore, no study has been carried out on drying followed by milling for micronization of the formed poly-ionic complex. Also, there were problems that active ingredient release is not readily controllable and active ingredient dissolution pattern depends on a pH due to properties of poly-ionic complex.

Therefore, there is still a need for a poly-ionic complex composition of chitosan and polyacrylic acid which has increased retention time in gastro-intestinal tract due to good mucoadhesiveness, well controlled drug release and decreased pH dependence of drug dissolution pattern as necessary, and can be produced by utilizing conventional pharmaceutical facilities, for example, to tablets by using a tableting machine.

CONTENTS OF THE INVENTION

Problems to be Solved

In an embodiment, the present disclosure provides a poly-ionic complex composition of chitosan and polyacrylic acid which has increased retention time in gastro-intestinal tract due to good mucoadhesiveness, well controlled drug release and decreased pH dependence of drug dissolution pattern as necessary, and can be produced by utilizing conventional pharmaceutical facilities, for example, to tablets by using a tableting machine.

In another embodiment, there is provided a mucoadhesive formulation comprising the poly-ionic complex.

Technical Means to Solve the Problems

The present disclosure provides a mucoadhesive pharmaceutical composition comprising an active ingredient and a poly-ionic complex (PIC) of chitosan and polyacrylic acid. The active ingredient may be in the form of particle such as powder, granule, pellet, crystalline solid, etc. The poly-ionic complex may be in the micronized form obtained by milling, for example, freeze milling, etc. The composition has good mucoadhesiveness, and thus it can be applied as various drug carriers such as oral formulation, buccal formulation, ophthalmic formulation, vaginal or rectal formulation, nasal formulation, ointment, etc. Particularly, as an oral formulation, it can be utilized as a gastro-intestinal retentive formulation, a sustained release oral formulation, etc. for an active ingredient having limited absorption region, since it has increased retention time in gastro-intestinal tract due to the mucoadhesiveness in gastro-intestinal tract and swelling property.

The present disclosure also provides a mucoadhesive pharmaceutical composition comprising an active ingredient, a poly-ionic complex of chitosan and polyacrylic acid, and a water soluble polymer. The active ingredient may be in the form of particle such as powder, granule, pellet, crystalline solid, etc. The poly-ionic complex may be in the micronized form obtained by milling, for example, freeze milling, etc. As the water soluble polymer, any gel-forming polymer can be used as long as it shows swelling property. For example, one or more of water soluble cellulose ether, polyethylene glycol, gelatin, alginate, dextrin, water soluble polyvinyl alcohol derivative or combinations thereof can be used, and for example, polyethylene oxide (PEO), hydroxyl propyl methyl cellulose (HPMC), hydroxyl propyl cellulose (HPC), etc. can be used. The composition has good mucoadhesiveness and strengthened swelling property, and in particular, it can act as a drug carrier having drug dissolution pattern in a pH independent manner.

The present disclosure also provides a mucoadhesive composition using, as a matrix, a mucoadhesive pharmaceutical composition comprising a poly-ionic complex of chitosan and polyacrylic acid and optionally a water soluble polymer, and further comprising an active ingredient with mucoadhesive coating. The composition adheres to mucous membranes in a living body, and can act as a drug carrier releasing an active ingredient over a long time, in particular, in a pH independent manner. The active ingredient may be in the form of particle such as powder, granule, pellet, crystalline solid, etc. In a particular embodiment, the active ingredient is coated with a mixture of chitosan and polyacrylic acid which are the components of the poly-ionic complex. Since the mixture of chitosan and polyacrylic acid, which is separately coated on active ingredient particles, has mucoadhesiveness in itself, the mucoadhesiveness to drug particles is doubled in addition to the mucoadhesiveness of the matrix, thereby maximizing the retention time in gastro-intestinal tract.

In an embodiment, the present disclosure provides a pharmaceutical composition and a pharmaceutical formulation comprising, as a drug carrier, a matrix obtained by adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; drying and milling, for example, freeze drying and freeze milling, the obtained poly-ionic complex to obtain micronized poly-ionic complex; and tableting the micronized poly-ionic complex.

In another embodiment, the present disclosure provides a pharmaceutical composition and a pharmaceutical formulation comprising, as a drug carrier, a matrix obtained by adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; drying and milling, for example, freeze drying and freeze milling, the obtained poly-ionic complex to obtain micronized poly-ionic complex; mixing the micronized poly-ionic complex with a water soluble polymer such as PEO, HPMC, HPC, etc.; and tableting the mixture.

In still another embodiment, the present disclosure provides a pharmaceutical composition and a pharmaceutical formulation comprising, as a drug carrier, a particle-containing matrix obtained by adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; drying and milling, for example, freeze drying and freeze milling the obtained poly-ionic complex to obtain micronized poly-ionic complex; mixing the micronized poly-ionic complex with mucoadhesive active ingredient particles separately coated with chitosan and polyacrylic acid, and tableting the mixture. In a particular embodiment, chitosan and polyacrylic acid are coated on the active ingredient particles by bottom spray coating in a fluidized bed reactor.

In still another embodiment, the present disclosure provides a pharmaceutical composition and a pharmaceutical formulation comprising, as a drug carrier, a particle-containing matrix obtained by adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; drying and milling, for example, freeze drying and freeze milling the obtained poly-ionic complex to obtain micronized poly-ionic complex; and mixing the micronized poly-ionic complex with a water soluble polymer such as PEO, HPMC, HPC, etc. and admixing thereto mucoadhesive active ingredient particles separately coated with chitosan and polyacrylic acid, and tableting the mixture. In a particular embodiment, chitosan and polyacrylic acid are coated on the active ingredient particles by bottom spray coating in a fluidized bed reactor.

In an embodiment, the composition and formulation are used as a mucoadhesive composition and formulation, for example, a mucoadhesive oral composition and formulation.

In addition, the present disclosure provides a method for preparing a mucoadhesive pharmaceutical composition, comprising:

(a) adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; and (b) drying and milling the obtained poly-ionic complex of chitosan and polyacrylic acid to obtain micronized poly-ionic complex; and optionally, (c) mixing the micronized poly-ionic complex with an active ingredient.

In one particular embodiment, the preparation method of the present disclosure further comprises coating the active ingredient with a mixture of chitosan and polyacrylic acid, and mixing the coated active ingredient with the micronized poly-ionic complex in step (c).

In another particular embodiment, the pH is adjusted to 5.0 to 6.0.

In another particular embodiment, the poly-ionic complex is freeze dried and freeze milled.

In another particular embodiment, the poly-ionic complex is micronized to have an average diameter of 1 nm to 300 μm.

In another particular embodiment, in the preparation method of the present disclosure, a water soluble polymer is further added and mixed in step (c). As the water soluble polymer, one or more of water soluble cellulose ether, polyethylene glycol, gelatin, alginate, dextrin, water soluble polyvinyl alcohol derivative or combinations thereof can be used, and for example, PEO, HPMC, HPC, etc. can be used.

Definition of Terms

Unless explicitly indicated otherwise, terms used herein throughout the specification can be defined as follows.

Unless especially mentioned otherwise, the term, "comprising" or "containing," used herein throughout the specification refers to including any element or component without special limitation, and it is not interpreted to exclude addition of other element or component.

The term, "active ingredient," may be a drug, i.e. a free base, its pharmaceutically acceptable salt, its isomer, or a mixture thereof.

The term, "polyacrylic acid," refers to a polymer having acrylic acid including linear, branched and crosslinked form, as its repeating unit, and includes ones with ionized carboxyl groups or various salt forms.

The term, "mucoadhesiveness," refers to a property adhering to mucous membranes through various interactions, inclusively comprising charge interaction, hydrogen bonding, Van der Waals bonding, viscosity interaction, etc.

The term, "micronized," includes powdered form of very small size, for example, having an average diameter in micrometer or nanometer size.

Mucoadhesive Pharmaceutical Composition

The pharmaceutical composition comprising a poly-ionic complex of chitosan and polyacrylic acid provided in the present disclosure has mucoadhesiveness, and thus it can be utilized in delivery of various drugs through mucous membranes. Specifically, there are various drug carriers such as oral formulation, buccal formulation, ophthalmic formulation, vaginal or rectal formulation, nasal formulation, ointment, etc. Particularly, as an oral formulation, it can be utilized as gastric retentive formulation retained in stomach by mucoadhesiveness, intestinal retentive formulation retained in small intestine by mucoadhesiveness, etc. It also has swelling property and thus can float in an environment like stomach, and can control the release of an active ingredient. Accordingly, the mucoadhesive pharmaceutical composition can be utilized as a sustained release oral formulation, a retentive formulation of an active ingredient having limited absorption region, and a bioavailability enhanced formulation of an active ingredient having a pH dependent solubility, etc.

In an embodiment, the mucoadhesive pharmaceutical composition is provided as a pharmaceutical composition comprising, as a drug carrier, a matrix obtained by adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; drying and milling, for example, freeze drying and freeze milling, the obtained poly-ionic complex to obtain micronized poly-ionic complex; mixing the micronized poly-ionic complex material with an active ingredient; and tableting the mixture.

Another embodiment of the present disclosure provides a pharmaceutical composition comprising, as a drug carrier, a particle-containing matrix obtained by adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; drying and milling, for example, freeze drying and freeze milling, the obtained poly-ionic complex to obtain a micronized poly-ionic complex; and mixing the micronized poly-ionic complex material with a water soluble polymer such as PEO, HPMC, HPC, etc. and an active ingredient, and tableting the mixture.

Still another embodiment of the present disclosure provides a pharmaceutical composition comprising, as a drug carrier, a particle-containing matrix obtained by adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; drying and milling, for example, freeze drying and freeze milling, the obtained poly-ionic complex to obtain a micronized poly-ionic complex; and mixing the micronized poly-ionic complex with active ingredient particles with mucoadhesive coating, and tableting the mixture. The mucoadhesive active ingredient particles can be obtained by coating the active ingredient with chitosan and polyacrylic acid by bottom spray coating in a fluidized bed reactor.

Still another embodiment of the present disclosure provides a pharmaceutical composition comprising, as a drug carrier, a particle-containing matrix obtained by adjusting pH of an acidic aqueous solution of chitosan and an aqueous solution of polyacrylic acid, respectively, and mixing them, or adjusting pH of a mixture of an acidic aqueous solution of chitosan and an aqueous solution of polyacrylic acid, to obtain a poly-ionic complex; drying and milling, for example, freeze drying and freeze milling the obtained poly-ionic complex to obtain a micronized poly-ionic complex; and mixing the micronized poly-ionic complex material with a water soluble polymer such as PEO, HPMC, HPC, etc. and mucoadhesive active ingredient particles, and tableting the mixture. The mucoadhesive active ingredient particles can be obtained by coating the active ingredient with chitosan and polyacrylic acid by bottom spray coating in a fluidized bed reactor.

Still another embodiment of the present disclosure provides a method for preparing the mucoadhesive pharmaceutical composition.

Poly-Ionic Complex

The poly-ionic complex comprises chitosan and polyacrylic acid.

Chitosan used in the present disclosure can have various ranges of molecular weight, and can be provided with various viscosities and various grades. In case of assessing the molecular weight based on the viscosity of chitosan, the range of the viscosity of chitosan may be within 5 cps to 50,000 cps when measured for chitosan solution with 0.5% concentration in 1% acetic acid solvent at 25° C. If the viscosity is lower than 5 cps, the molecular weight of chitosan is too low and thus it may be difficult to obtain a stable poly-ionic complex. If the viscosity is higher than 50,000 cps, there may be a problem in production due to too high viscosity. The viscosity of chitosan may be in a range of 50 cps to 40,000 cps, 100 cps to 30,000 cps, 200 cps to 20,000 cps, or 500 cps to 10,000 cps. The deacetylation degree of chitosan may be 60% or higher, 70% or higher, 75% or higher, or 80% or higher. If the deacetylation degree is low, the solubility decreases, and the formation of poly-ionic complex becomes difficult due to the lack of functional groups.

Polyacrylic acid used in the present disclosure can have various forms such as linear, branched, or crosslinked form, etc. and in case of linear or branched form, the molecular weight may be 50,000 to 6,000,000. If the molecular weight is lower than 50,000, the stability of poly-ionic complex in a solvent decreases due to too low molecular weight. If the molecular weight is higher than 6,000,000, there may be a problem in production due to too high molecular weight. In case of linear or branched form, the molecular weight of the polyacrylic acid may be 200,000 to 5,000,000, 400,000 to 4,000,000, 800,000 to 3,000,000, or 1,000,000 to 2,000,000. In case of crosslinked form, it may be named Carbomer, Carbopol, etc. and may be crosslinked by aryl sucrose or aryl ether of pentaerythritol. Examples thereof include Carbomer 934, Carbomer 934P, Carbomer 940, Carbomer 941, Carbomer 971P, Carbomer 974P, Carbomer 1342, etc. but it is not limited thereto. In case of crosslinked polymer, the molecular weight is difficult to obtain, and presumed to be $7 \times 10^5$ to $4 \times 10^9$ theoretically, but there is no specific limitation. Regardless of linear, branched or crosslinked form, the polyacrylic acid may be in the form of an alkali metal salt. In a particular embodiment, it may be sodium salt.

The ratio of chitosan and polyacrylic acid used for preparing the poly-ionic complex may be 1:0.1 to 1:10 by weight. If the ratio is less than 1:0.1 or greater than 1:10, either cations or anions prevail, and thus it is difficult to form a poly-ionic complex. The ratio may be 1:0.2 to 1:5. The ratio may be 1:0.3 to 1:2. The ratio may be 1:0.3 to 1:1.

The poly-ionic complex can be dried by air drying, ambient temperature drying, vacuum drying, heat drying, freeze drying, etc. Vacuum drying, heat drying or freeze drying may be used. Vacuum drying or freeze drying may be used.

The poly-ionic complex can be micronized by various methods such as freeze mill, wet mill, ball mill, air mill, jet mill, etc. In particular, micronization by freeze mill forms microstructures on the surface, and thus it can improve the efficacy of formulation.

Specifically, the poly-ionic complex of the present disclosure can be prepared by the following method. Chitosan is dissolved in an acidic aqueous solution and polyacrylic acid is dissolved in water, and the two solutions are mixed and the pH is adjusted. Then, the resulting mixture is dried and milled to obtain micronized powder. More specifically, for example, chitosan is dissolved in dilute acetic acid or dilute HCl aqueous solution, and polyacrylic acid is dissolved or dispersed in water. The two solutions are mixed with agitation, and the pH is adjusted to about 5.0 to 6.0, or about 5.5, using dilute sodium hydroxide to obtain poly-ionic complex precipitate. The precipitate is separated by centrifugation and removal of supernatant, collected after freeze drying or vacuum drying, and milled to obtain micronized powder.

In another embodiment, after preparing the solutions of chitosan and polyacrylic acid, their pH is adjusted identically, and then the two solutions are mixed to form poly-ionic complex directly, and the formed poly-ionic complex is dried and milled to obtain micronized powder. More specifically, for example, chitosan is dissolved in dilute HCl or dilute acetic acid aqueous solution and the pH is adjusted to about 5.0 to 6.0, or about 5.5, using dilute sodium hydroxide solution. Polyacrylic acid is dissolved in water and the pH is adjusted identically with that of the aqueous chitosan solution, i.e., to about 5.0 to 6.0, or about 5.5, using dilute sodium hydroxide solution. Then, the aqueous polyacrylic acid solution is added to the chitosan solution and mixed to form a poly-ionic complex. Both components can be fed at a constant rate by using a peristaltic pump, etc. and the poly-ionic complex can be formed more uniformly by feeding the aqueous polyacrylic acid solution to the chitosan solution under agitation with a mechanical stirrer. The precipitate is collected and washed with water of pH adjusted to about 5.0 to 6.0, or about 5.5, and washed again with distilled water 2 to 3 times. It may be freeze dried or vacuum dried to obtain the poly-ionic complex, and then milled to obtain micronized powder.

If the pH is lower than 5.0, the ionization degree of the carboxyl group of polyacrylic acid is insufficient to form unstable poly-ionic complex. If the pH is higher than 6.0, the ionization degree of the amine group of chitosan is insufficient to form unstable poly-ionic complex, too. In addition, the poly-ionic complex of the present disclosure may be micronized to have an average diameter of approximately 1 nm to 300 μm. If the average diameter is greater than 300 μm, it may be difficult to form a uniform matrix and disintegration of tablets may be accelerated. If the average diameter is less than 1 nm, it may not be easily handled. Micronization may be performed to a size of 200 μm or less, 100 μm or less, 50 μm or less, or 10 μm or less. The micronized poly-ionic complex of the present disclosure has improved properties due to its unique structural, physical and chemical features.

Matrix Tablet

A matrix tablet can be obtained by mixing the micronized poly-ionic complex of chitosan and polyacrylic acid with an active ingredient, and tableting the mixture. Such a tablet has swelling property and mucoadhesiveness. For tableting the micronized poly-ionic complex of chitosan and polyacrylic acid, it may be granulated by wet granulation, dry granulation, etc.

If the micronized poly-ionic complex of chitosan and polyacrylic acid is mixed with a water soluble polymer, swelling property is maximized while maintaining mucoadhesiveness, and active ingredient release can be controlled. In particular, a pH dependent dissolution can be improved, and thus an active ingredient can be consistently released even though the pH in gastro-intestinal tract varies depending on foods or individuals. The water soluble polymer may be water soluble cellulose ether such as hydroxypropyl cellulose, hydroxypropyl methylcellulose (hypromellose), hydroxyethyl cellulose, etc., polyethylene oxide (PEO), gelatin, alginate, dextrin, water soluble polyvinyl alcohol derivative such as polyvinyl alcohol-acrylic acid-methyl methacrylate copolymer, polyvinyl alcohol-polyethylene glycol graft copolymer, etc. One or two or more selected from water soluble cellulose ether or polyethylene glycol may be used. One or two or more selected from hydroxypropyl cellulose, hydroxypropyl methylcellulose, or polyethylene oxide may be used. A polymer of relatively high viscosity may be used. For example, in case of hydroxypropyl cellulose or hydroxypropyl methylcellulose, the viscosity measured for 0.5% aqueous solution at 25° C. may be 10,000 cps or higher, 50,000 cps or higher, or 100,000 cps or higher. In case of polyethylene oxide, the molecular weight may be 100,000 or higher, 1,000,000 or higher, or 3,000,000 or higher. If the viscosity or molecular weight is lower than the above, tablets disintegrate rapidly and can hardly maintain the mucoadhesiveness.

The amount of water soluble polymer may be 2 to 80%, based on the total weight of tablet. If the amount is greater than 80%, mucoadhesiveness of the poly-ionic complex may be limited. If the amount is less than 2%, the water soluble polymer may not function. The amount may be 10 to 60%. The amount may be 15 to 50%.

In the matrix tablet, in order to improve physical property, producibility, compressibility, appearance, taste, drug stability, etc. of the tablet, various additives can be mixed. For example, the additive may be stabilizer, surfactant, solubilizing agent, sweetener, flavor enhancer, pigment, wetting agent, filler, lubricant, buffer, adsorbent, binder, suspending agent, hardener, antioxidant, glossing agent, fragrance, flavor, coating agent, moisture controlling agent, anti-foaming agent, refreshing agent, masticating agent, antistatic agent, coloring agent, sugarcoating agent, isotonic agent, softener, emulsifier, adhesive, thickener, foaming agent, pH controlling agent, excipient, dispersant, disintegrating agent, waterproof agent, antiseptic agent, preservative, solubilizing aid, solvent, fluidizing agent, etc., but it is not limited thereto, and any one can be used as long as it is pharmaceutically acceptable.

In a particular embodiment, the mucoadhesive pharmaceutical composition of the present disclosure may further comprise disintegrating agent or lubricant, etc. The disintegrating agent may be starch, cellulose, crosslinked polymer, for example, crosslinked polyvinylpyrrolidone or crospovidone, for example, POLYPLASDONE XL manufactured by International Specialty Products, USA; crosslinked carboxymethyl cellulose sodium or croscarmellose sodium, for example, AC-DI-SOL manufactured by FMC; and crosslinked carboxymethyl cellulose calcium, etc., but it is not limited thereto. The lubricant may be one or two or more selected from the group consisting of stearic acid, glyceryl behenate, glyceryl mono stearate, magnesium stearate, calcium stearate, silicon dioxide, talc, magnesium silicate, sodium stearyl fumarate, etc., but it is not limited thereto.

Active Ingredient

The active ingredient may comprise one or more selected from the group consisting of a drug, its pharmaceutically acceptable salt, and its isomer.

There is no special limitation to the applicable active ingredient. For example, the active ingredient which can be formulated as the mucoadhesive pharmaceutical composition of the present disclosure may be one or more selected from the group consisting of the following, but it is not limited thereto:

Antipsychotic drugs such as chlorpromazine, thioridazine, loxapine, molindone, clozapine, olanzapine, quetiapine, risperidone, ziprasidone, fluphenazine, haloperidol, perphenazine, trifluoperazine, pimozide, aripiprazole, prochlorperazine, tiotixene, paliperidone, etc.;

Antidepressant drugs such as mirtazapine, bupropion, amoxapine, phenelzine, tranylcypromine, citalopram, fluoxetine, fluvoxamine, paroxetine, sertraline, venlafaxine, maprotiline, trazodone, nefasodone, amitriptyline, clomipramine, desipramine, dexepin, imipramine, nortriptyline, protriptyline, trimipramine, etc.;

Drugs for degenerative neuronal disease such as amantadine, benztropine mesylate, carbidopa and levodopa, donepezil, bromocriptine, pergolide, pramipexole, ropinirole, etc.;

Anti-ADHD (attention deficit hyperactivity disorder) drugs such as methylphenidate, atomoxetine, etc.;

Anticonvulsant drugs such as pregabalin, lacosamide, carbamazepine, clonazepam, ethosuximide, felbamate, gabapentin, lamotrigine, levetiracetam, oxcarbazepine, phenobarbital, phenytoin, primidone, tiagabine, topiramate, valproic acid, divalproex sodium, zonisamide, etc.;

Antianxiety drugs, sedatives or sleeping drugs such as alprazolam, lorazepam, oxazepam, chlordiazepoxide, clorazepate, diazepam, halazepam, midazolam, triazolam, zaleplon, zolpidem, estazolam, temazepam, flurazepam, quazepam, meprobamate, phenobarbital, chloral hydrate, ethchlorvinol, glutethimide, pentobarbital, secobarbital, etc.;

Drugs for erectile dysfunction such as sildenafil, vardenafil, alprostadil, tadalafil, mirodenafil, udenafil, etc.;

Immunodepressant drugs such as azathioprine, cyclosporine, mycophenolate mofetil, sirolimus, tacrolimus, everolimus, etc.;

Antihypertensive drugs such as doxazosin mesylate, prazosin hydrochloride, terazosin hydrochloride, benazepril, captopril, clonidine hydrochloride, enalapril, hydralazine hydrochloride, labetalol hydrochloride, losartan potassium, methyldopate hydrochloride, minoxidil, moexipril, trandolapril, candesartan, irbesartan, losartan, telmisartan, valsartan, guanabenz acetate, guanadrel sulfate, guanfacine hydrochloride, reserpine, etc.;

Beta-adrenaline blockers such as acebutolol, atenolol, betaxolol, bisoprolol, carteolol, carvedilol, labetalol, metoprolol, nadolol, penbutolol, pindolol, propranolol, sotalol, timolol, etc.;

Calcium-channel blockers such as amlodipine, bepridil, diltiazem, felodipine, isradipine, nicardipine, nifedipine, nimodipine, nisoldipine, verapamil, etc.;

Lipid lowering drugs such as fenofibrate, gemfibrozil, niacin, atorvastatin, fluvastatin, lovastatin, pravastatin, simvastatin, etc.;

Gastrointestinal motility drugs such as mosapride, itopride, domperidone, trimebutine, metoclopramide, bisacodyl, diphenoxylate hydrochloride and atropine sulfate, docusate salt, loperamide, magnesium salt, ursodiol, etc.;

Coagulants and anticoagulants such as clopidogrel bisulfate, phytonadione, ticlopidine, warfarin sodium, etc.;

Vasodilators such as limaprost, beraprost, sarpogrelate, etc.;

Antimigraine drugs such as almotriptan, ergotamine tartrate, frovatriptan, methysergide maleate, sumatriptan succinate, zolmitriptan, etc.;

Antirheumatic drugs such as auranofin, azathioprine, cyclosporine, hydroxychloroquine sulfate, leflunomide, methotrexate, penicillamine, sulfasalazine, etc.;

Antiinflammatory drugs such as acetaminophen, aspirin, diclofenac, etodolac, fenoprofen, ibuprofen, ketoprofen, naproxen, indomethacin, ketorolac, sulindac, tolmetin, meclofenamate, mefenamic acid, nabumetone, meloxicam, piroxicam, celecoxib, rofecoxib, etc.;

Opioids such as buprenorphine, codeine, fentanyl, hydrocodone, hydromorphone, levorphanol, meperidine, morphine, oxycodone, pentazocine, propoxyphene, etc.;

Non-opioid analgesics such as tramadol, tapentadol, etc.;

Anticancer drugs such as imatinib, erlotinib, sunitinib, sorafenib, lapatinib, gefitinib, dasatinib, lenalidomide, nilotinib, crizotinib, pazopanib, vandetanib, axitinib, regorafenib, apatinib, vemurafenib, ruxolitinib, temozolomide, radotinib, everolimus, etc.;

Antimycobacterial drugs such as aminosalicylic acid salts, clofazimine, cycloserine, ethionamide, rifabutin, etc.;

Antiparasitic drugs such as albendazol, ivermectin, mebendazol, praziquantel, etc.;

Antiviral drugs such as valacyclovir, didanosine, famciclovir, valganciclovir, indinavir, lamivudine, nelfinavir mesylate, nevirapine, ritonavir, stavudine, oseltamivir phosphate, etc.;

Beta-lactams such as amoxicillin, amoxicillin and potassium clavulanate, ampicillin, cefuroxime sodium, cefuroxime axetil, penicillin G and Y salts, cefditoren, cefixime, cloxacillin sodium, dicloxacillin sodium, etc.;

Macrolide antibiotics such as erythromycin estolate, erythromycin ethylsuccinate, erythromycin stearate, etc.;

Fluoroquinolones such as ciprofloxacin, enoxacin, etc.;

Tetracyclines such as demeclocycline hydrochloride, doxycycline calcium, tetracycline, tetracycline hydrochloride, etc.;

Alkylating agents such as altretamine, busulfan, chlorambucil, melphalan, cyclophosphamide, procarbazine hydrochloride, temozolomide, etc.;

Antimetabolites such as methotrexate, mercaptopurine, thioguanine, etc.;

Hormonal drugs and antagonists such as bicalutamide, flutamide, nirutamide, aminoglutethimide, anastrozole, exemestane, letrozole, tamoxifen citrate, toremifene citrate, etc.;

Mitotic inhibitors such as etoposide phosphate, etc.;

Antiarrhythmic drugs such as amiodarone hydrochloride, digoxin, disopyramide phosphate, dofetilide, flecainide acetate, mexiletine hydrochloride, moricizine hydrochloride, procainamide hydrochloride, propafenone hydrochloride, quinidine sulfate, quinidine gluconate, sotalol hydrochloride, tocainide, etc.;

Nitrates such as isosorbide dinitrate, nitroglycerin, nitroprusside sodium, etc.;

Antiglaucoma ophthalmic drugs such as acetazolamide, dichlorphenamide, methazolamide, etc.;

Drugs for treating acid-peptic disease such as aluminum carbonate, aluminum hydroxide, magnesium hydroxide, sodium bicarbonate, calcium carbonate, magaldrate, bismuth salts, cimetidine, famotidine, nizatidine, ranitidine, misoprostol, lansoprazole, omeprazole, pantoprazole, rabeprazole, sucralfate, etc.;

Antiemetics such as buclizine, cyclizine, dimenhydrinate, diphenhydramine, meclizine, dronabinol, chlorpromazine, perphenazine, prochlorperazine, promethazine, thiethylperazine, triflupromazine, dolasetron, granisetron, ondansetron, dexamethasone, lorazepam, granisetron, ramosetron, aprepitant, etc.;

Hematopoietic drugs such as iron salts, etc.;

Adrenal hormones such as cortisone, hydrocortisone, methylprednisolone, prednisone, triamcinolone, betamethasone, dexamethasone, fludrocortisone, etc.;

Antidiabetic drugs such as acarbose, metformin, nateglinide, repaglinide, acetohexamide, chlorpropamide, tolazamide, tolbutamide, glimepiride, glipizide, glyburide, pioglitazone, rosiglitazone, etc.;

Contraceptives such as norethindrone, norgestrel, levonorgestrel, etc.;

Female sex hormones such as estradiol and esters thereof, estrogen, estropipate, medroxyprogesterone, mifepristone, norethindrone acetate, progesterone, raloxifene, etc.;

Thyroid and antithyroid drugs such as iodide, levothyroxine sodium, liothyronine sodium, liotrix, methimazole, propylthiouracil, etc.;

Diuretics such as amyloid hydrochloride, bumetanide, ethacrynic acid, furosemide, torasemide, hydrochlorothiazide, chlorthiazide, chlorthalidone, indapamide, metolazone, polythiazide, quinthazone, trichomethiazide, spironolactone, triamterene, etc.;

Electrolytes such as chelated magnesium, magnesium chloride, magnesium hydroxide, magnesium oxide, potassium salts, etc.;

Drugs for treating gout such as allopurinol, colchicine, probenecid, sulfinpyrazone, etc.;

Drugs for treating asthma such as albuterol sulfate, montelukast sodium, theophylline, zileuton, etc.;

Antihistamines such as acrivastine, azatadine, brompheniramine maleate, carbinoxamine maleate, cetirizine hydrochloride, chlorpheniramine maleate, diphenhydramine hydrochloride, clemastine fumarate, cyproheptadine hydrochloride, fexofenadine, hydroxyzine, loratadine, desloratadine, etc.;

Drugs for suppressing cough or drugs for treating cold, such as dextromethorphan hydrobromide, guaifenesin, pseudoephedrine hydrochloride, etc.; and Health Foods.

The active ingredient may be applied in various forms. The active ingredient may be in various forms such as powder like micronized powder or flour, etc., particles like microcrystalline solid, microparticles, etc., granule, spherical, cylindrical, pellet, etc. In a particular embodiment, it may be micronized to nano-to micro-size and included in the matrix. It may be included in the matrix as the drug alone or in a granulated form which is prepared by mixing the drug with additives and granulating the mixture, or granulating the drug and the poly-ionic complex together, or granulating the drug and the water soluble polymer. The drug may be coated on a spherical seed such as sugar sphere or microcrystalline cellulose sphere. It may be prepared in the form of pellets by melt extrusion.

Granules, coated ones on spherical seed, or pellets may be further coated with a polymer for taste masking, dissolution control, stability improvement, etc. Particularly, for active ingredient release control, a water insoluble polymer may be coated to form a release control membrane.

Granules, coated ones on spherical seed, or pellets, or additionally polymer-coated ones may finally be coated with the components for forming the mucoadhesive poly-ionic complex. In this case, drug granules, particles or pellets themselves have mucoadhesiveness in addition to the mucoadhesiveness imparted by the matrix, mucoadhesiveness may be doubled to maximize the effect. Even after the matrix disintegrates, drug-containing granules, particles or pellets have their own mucoadhesiveness.

For coating the components for forming the mucoadhesive poly-ionic complex on drug-containing granules, particles or pellets, for example, chitosan is dissolved in a dilute HCl solution, and thereto an aqueous solution of polyacrylic acid is added to form a mixture, and the mixture is sprayed onto a fluidized bed coater, while fluidizing drug-containing granules, particles or pellets. The obtained coated product has mucoadhesiveness, and the coating membrane can be maintained for 12 hours or longer even in an acidic aqueous solution, to show mucoadhesiveness.

Conditions, features and mixing ratio of chitosan and polyacrylic acid used for the mucoadhesive coating are the same as, or similar to, those of chitosan and polyacrylic acid used for forming the poly-ionic complex. The coating ratio can be calculated from the weight of the coated poly-ionic complex-forming components with regard to the weight of pre-coated formulation. The coating ratio of the poly-ionic complex-forming components may be from 2% to 50%, from 4% to 30%, or from 5% to 15%. If the coating ratio is less than 2%, it may be difficult to coat the seed uniformly. If the coating ratio is greater than 50%, the coating takes too long time.

The mucoadhesive coating layer may have an average thickness of 2 to 100 μm, 3 to 50 μm, or 5 to 30 μm. The average thickness may be 2 μm or greater in order to effectively show the mucoadhesive effect, and 100 μm or less in order to reduce the coating time and facilitate the drug release.

The mucoadhesive coating layer may be formed from a coating solution wherein chitosan and polyacrylic acid are mixed in a solvent. The solvent may be selected from the group consisting of water, linear or branched alcohols having 1 to 4 carbon atoms, for example, methanol, ethanol, isopropyl alcohol, propanol, and the like. The concentration of the poly-ionic complex-forming components in the coating solution may be 0.005 to 10% by weight.

In an embodiment, the mucoadhesive coating layer may be formed through coating the coating solution of poly-ionic complex-forming components on the surface of granules, particles or pellets by using a conventional machine such as coater, fluidized bed coater, fluidized bed processer, or fluidized bed granulator, etc. Specifically, a fluidized bed system with bottom spray, a centrifugal granulator, Granurex® (manufacture by Freund), etc. may be used.

The mucoadhesive coating layer may further comprise various biologically inert agents other than the poly-ionic complex-forming components for additional purposes such as efficiency of coating, stability of active ingredient, appearance, color, protection, maintenance, efficacy improvement, production process improvement or auxiliary release control.

As the biologically inert agent, one or more selected from the group consisting of plasticizer, lubricant, surfactant, glidant, anti-foaming agent, coloring agent, fragrance, sweetener, stabilizer, antioxidant, paraffin, wax, etc. may be used.

In order to ensure the stability of active ingredient, coating may be performed to separate the mucoadhesive coating layer from the active ingredient layer. A water soluble polymer may be coated to have no effect on active ingredient dissolution.

In order to additionally control the dissolution of active ingredient, a dissolution control layer may be coated between the mucoadhesive coating layer and the active ingredient layer. The dissolution control layer may comprise a water insoluble polymer. The water insoluble polymer may be ethyl cellulose, ammonium methacrylate copolymer, polyvinyl acetate, etc. It may comprise ammonium methacrylate copolymer. The water insoluble ammonium methacrylate copolymer may be poly(ethyl acrylate/methyl methacrylate/chlorinated trimethylammonium methacrylate). The water insoluble ammonium methacrylate copolymer may have a molecular weight ranging from 20,000 to 500,000.

In an embodiment, the water insoluble ammonium methacrylate copolymer may show variable water permeability depending on the weight ratio of chlorinated trimethylammonium methacrylate unit. For example, the water insoluble ammonium methacrylate copolymer may be one having chlorinated trimethylammonium methacrylate unit of 8.85 to 11.96% by weight (for example, commercial name of Eudragit® RL, Evonik) or 2.0 to 7.99% by weight (for example, commercial name of Eudragit® RS, Evonik), based on the total weight of the copolymer, or a mixture thereof.

As water insoluble ammonium methacrylate copolymer has a larger amount of chlorinated trimethylammonium methacrylate unit, it shows faster water permeation or active ingredient release. As it has a smaller amount of chlorinated trimethylammonium methacrylate unit, it shows slower water permeation or active ingredient release. For example, one with chlorinated trimethylammonium methacrylate unit of 8.0 to 15.0% by weight, for example, commercial name of Eudragit® RL, Evonik, has relatively faster water permeation or active ingredient release, and one with chlorinated trimethylammonium methacrylate unit of 2.0 to 7.99% by weight, for example, commercial name of Eudragit® RS, Evonik, has relatively slower water permeation or active ingredient release.

Effects of the Invention

The mucoadhesive pharmaceutical composition comprising micronized powder of poly-ionic complex (PIC) of chitosan and polyacrylic acid in the present disclosure has good mucoadhesiveness, and thus it can be used as various drug carriers such as oral formulation, buccal formulation, ophthalmic formulation, vaginal or rectal formulation, nasal formulation, ointment, etc. Particularly, as oral formulation, since it has increased retention time in gastro-intestinal tract due to the mucoadhesiveness in gastro-intestinal tract and swelling property, it can be utilized as gastro-intestinal retentive formulation, sustained release oral formulation, etc. of an active ingredient having limited absorption region.

BEST MODE FOR CARRYING OUT THE INVENTION

Hereinafter, examples are provided to facilitate the understanding of the present invention. However, the following examples seek to illustrate the present invention only, and the scope of the present invention is not limited thereto in any manner.

In the following examples, analyses were carried out with reference to the following Reference Examples 1 to 5.

Reference Example 1: Dissolution Test

Dissolution test of an active ingredient from the formulation was conducted according to Method 2 Paddle Method of "36. Dissolution Test Method" in Korean Pharmacopoeia $8^{th}$ edition (KP VIII). The eluent was selected from a buffer of pH 1.2, a buffer of pH 4.0, a buffer of pH 6.8, water and 0.1N HCl, and used in an amount of 900 ml. The test was conducted at 37° C. with 100 rotations per minute.

After dissolution, analysis of drug was conducted by using high performance liquid chromatography (HPLC). Analysis of drug was performed under conventionally known conditions.

For example, when the active ingredient was paliperidone, the following conditions were used for the analysis:
Mobile phase: A mixed solution of a solution prepared by dissolving 21.76 g of potassium phosphate monobasic in 4 L of water and adjusting the pH to 2.0 with phosphoric acid, and 1 L of acetonitrile
Column: XBridge phenyl. 150×4.6 mm, 3.5 μm
Flow rate: 1.0 ml/min
Column Temperature: 27° C.
Wavelength: 238 nm
Injection volume: 10 μl When the active ingredient was tamsulosin HCl, the following conditions were used for the analysis:
Mobile phase: A solution prepared by dissolving 8.7 mL of perchloric acid and 3.0 g of sodium hydroxide in 1900 mL of water, adjusting the pH to 2.0 with sodium hydroxide, adding water thereto to make the volume 2000 mL, and taking 1400 mL of this solution and adding 600 mL of acetonitrile thereto
Column: Octadecyl silylated silica gel packing 150×4.6 mm, 5 μm
Flow rate: 1.0 ml/min
Column Temperature: 40° C.
Wavelength: 225 nm
Injection volume: 100 μl Reference Example 2: Preparation of Disc In order to test the mucoadhesiveness of the matrix-forming agent, the sample was prepared in disc form using a die to make disc for measuring IR (Infrared) spectrum. 100 mg of the sample was put into a die for preparing KBr disc and 5 to 10 tons of pressure was maintained for 3 minutes, and then a compressed disc with diameter of about 12 mm and thickness of about 0.75 mm was obtained.

Reference Example 3: In Vitro Mucoadhesiveness Test

The in vitro test for mucoadhesiveness was conducted by utilizing a texture analyzer.

A probe with diameter of 5 mm was used. The sample was fixed to the probe with double-sided tape, and cellulose acetate membrane filter was fixed at the lower part with double-sided tape and wetted with 100 μl of 3% mucin solution to simulate the environment of gastro-intestinal tract. Mucin was dissolved in a buffer of pH 1.2 or distilled water to make 3% solution for use. The measurement was made 1 minute after the wetting of the membrane. The descending speed of the probe was 0.5 mm/s, the pressing force of 1 N was maintained for 30 seconds, and then, the ascending speed was 0.5 mm/s, to measure mucoadhesiveness. The result is shown as adhesion force (N).

(Reference: Int J Pharm Sci Drug Res, 2011, 3, 84~88, Eur J Pharm Biopharm, 2009, 71, 325-331)

The disc prepared according the method disclosed in Reference Example 2 was cut into a size of 2.5 mm×2.5 mm and attached to the probe to measure mucoadhesiveness (adhesion force), and the result was recorded in N unit.

Reference Example 4: Ex Vivo Mucoadhesiveness Test

Everted sac method was used to measure the mucoadhesiveness ex vivo. Small intestine of rat was everted and saline was filled therein to make intestinal sac, and the adhesion time was measured. Specifically, a rat was sacrificed. Small intestine was extracted therefrom, cut into a length of about 10 cm and everted. The lower part was tied and saline was filled therein, and the upper part was tied to make intestinal sac for use. The prepared intestinal sac was placed in a plastic tube and the empty space was filed with saline. As samples, the test material was cut into 20 pieces of a small size and put into the plastic tube and rotated at 300 rpm in a shaking bath, and detached samples were counted over time. In order to secure reproducibility, the test was repeated 3 times for the test material. Discs prepared in Reference Example 2 were cut into a size of about 1 mm×about 2 to 3 mm, and tested. Mucoadhesive pellets, particles or granules containing an active ingredient were used as the sample and tested regardless of shape and size, without additional treatment. The number of the attached samples over time was represented in %.

Reference Example 5: Residual Ratio Test in an Acidic Environment

The disc sample prepared in Reference Example 2 was attached on a slide glass with double-sided tape. The disc was placed at a point having a distance of about 5 mm from one end of the slide glass. Into a 100 mL beaker, 50 mL of pH 1.2 buffer was poured, and the slide glass with the attached disc was fixed on the wall of the beaker by using strong double-sided foam tape while the disc was faced to the inside and immersed in the pH 1.2 buffer. The solution was stirred with a hexagonal magnetic stirrer of a length of about 2.85 cm at 120 rpm for 2 hours, and then the sample with the slide glass was dried in an oven at 40° C. The total residual amount of the sample was measured by comparing the weight of the sample before starting the test and the weight of the sample after drying, and the residual ratio in an acidic solution was calculated by the following equation.

$$\text{Residual ratio (\%)} = \frac{\text{Total weight before test (mg)} - \text{Total weight after test (mg)}}{\text{Sample weight before test (mg)}} \times 100$$

EXAMPLES

Example 1: Preparation of a Poly-Ionic Complex of Chitosan and Polyacrylic Acid 5 g of chitosan (Biopolytec, viscosity: 200 cps, deacetylation degree: 82.2%) was dissolved in 2.5 L of distilled water with 10 ml of concentrated hydrochloric acid. 5 g of polyacrylic acid (Aldrich, molecular weight: 1,250,000) was dissolved in 5 L of distilled water. The two solutions were mixed and the pH was adjusted to about 5.5. The precipitate was separated by centrifugation (3000 rpm, 20 minutes) and discarding the supernatant, and washed 2 or 3 times with water of about pH 5.5, and then freeze dried. The obtained poly-ionic complex was freeze milled to a size of 100 μm or less to give micronized powder of poly-ionic complex having microstructure.

Poly-ionic complexes were prepared according to substantially the same method, with varying the kind and molecular weight (Mw), ratio, etc. of chitosan and polyacrylic acid as shown in the following table, discs were formed according to the method of Reference Example 2, and in vitro mucoadhesiveness test was conducted according to the method of Reference Example 3. The results are shown below.

TABLE 1

| Sample | Chitosan | Polyacrylic acid | Ratio | Adhesion force (N) | Yield (%) |
|---|---|---|---|---|---|
| PIC-01 | Chitosan 200 cps (Biopolytec) | Polyacrylic acid Mw 1,250,000 (Aldrich) | 1:1 | — | — |
| PIC-02 | Chitosan 200 cps (Biopolytec) | Polyacrylic acid Mw 1,250,000 (Aldrich) | 2.35:1 | — | 73.7 |
| PIC-03 | Chitosan 200 cps (Biopolytec) | Polyacrylic acid Mw 1,250,000 (Aldrich) | 4:1 | — | — |
| PIC-04 | Chitosan 200 cps (Biopolytec) | Polyacrylic acid Mw 1,250,000 (Aldrich) | 2.35:1 | — | 92.9 |
| PIC-05 | Chitosan 200 cps (Biopolytec) | Polyacrylic acid Mw 3,000,000 (Aldrich) | 2.35:1 | — | 48.3 |
| PIC-06 | Chitosan 10 cps (Biopolytec) | Polyacrylic acid Mw 1,250,000 (Aldrich) | 2.35:1 | 1.193 | 53.77 |
| PIC-07 | Chitosan 200 cps (Biopolytec) | Polyacrylic acid Mw 1,250,000 (Aldrich) | 2.35:1 | 1.221 | 73.76 |

TABLE 1-continued

| Sample | Chitosan | Polyacrylic acid | Ratio | Adhesion force (N) | Yield (%) |
|---|---|---|---|---|---|
| PIC-08 | Chitosan 1000 cps (Biopolytec) | Polyacrylic acid Mw 1,250,000 (Aldrich) | 2.35:1 | 1.428 | — |
| PIC-09 | Chitosan 1000 cps (Biopolytec) | Carbomer 934P | 2.35:1 | — | 70.4 |
| PIC-10 | DiChitosan H (Dainichiseika) | Polyacrylic acid Mw 1,250,000 (Aldrich) | 2.35:1 | 1.239 | 86.9 |
| PIC-11 | DiChitosan VH (Dainichiseika) | Polyacrylic acid Mw 1,250,000 (Aldrich) | 2.35:1 | 0.934 | — |
| PIC-12 | Chitosan (Aldrich) | Polyacrylic acid Mw 1,250,000 (Aldrich) | 2.35:1 | 1.295 | 88.8 |
| PIC-13 | Chitopharm L (Chitinor) | Polyacrylic acid Mw 1,250,000 (Aldrich) | 2.35:1 | 1.243 | 70.8 |
| PIC-14 | Chitopharm M (Chitinor) | Polyacrylic acid Mw 1,250,000 (Aldrich) | 2.35:1 | 1.254 | — |

As can be seen from the above table, the poly-ionic complex of the present disclosure showed good mucoadhesiveness. In addition, in case of PIC-08 and PIC-09, all of 20 pieces were adhered for 24 hours in ex vivo mucoadhesiveness test of Reference Example 4.

Example 2: Preparation of a Poly-Ionic Complex of Chitosan and Polyacrylic Acid 11.75 g of chitosan (Biopolytec, viscosity: 1000 cps, deacetylation degree: 82.2%) was dissolved in 5.8 L of distilled water with 23.5 ml of concentrated hydrochloric acid, and the pH was adjusted to about 5.5 by using 1M NaOH aqueous solution. 5 g of polyacrylic acid (Aldrich, molecular weight: 1,250,000) was dissolved in 5 L of distilled water, and the pH was adjusted to about 5.5 by using 1M NaOH aqueous solution. The two solutions were mixed to form precipitate. The formed precipitate was separated by centrifugation (3000 rpm, 20 minutes) and discarding the supernatant, and washed 2 or 3 times with water of about pH 5.5, and then freeze dried. The obtained poly-ionic complex obtained was freeze milled to a size of 10 μm or less to give micronized powder of poly-ionic complex having microstructure.

Poly-ionic complexes were prepared according to substantially the same method, with varying the kind and molecular weight (Mw) of chitosan and polyacrylic acid as shown in the following table, discs were formed according to the method of Reference Example 2, and in vitro mucoadhesiveness test was conducted according to the method of Reference Example 3. The results are shown below.

TABLE 2

| Sample | Chitosan | Polyacrylic acid | Ratio | Adhesion force (N) | Yield (%) |
|---|---|---|---|---|---|
| PIC-15 | Chitosan 1000 cps (Biopolytec) | Polyacrylic acid Mw 1,250,000 (Aldrich) | 2.35:1 | 1.101 | 54.70% |
| PIC-16 | Chitosan 1000 cps (Biopolytec) | Polyacrylic acid Mw 1,250,000 (Aldrich) | 1.47:1 | — | 72.30% |
| PIC-17 | Chitosan 1000 cps (Biopolytec) | Polyacrylic acid Mw 1,250,000 (Aldrich) | 1.11:1 | 1.116 | 96.60% |
| PIC-18 | Chitosan 1000 cps (Biopolytec) | Polyacrylic acid Mw 1,250,000 (Aldrich) | 0.74:1 | — | 98.00% |
| PIC-19 | Chitosan 1000 cps (Biopolytec) | Carbomer 934P | 2.22:1 | 1.423 | 87.00% |
| PIC-20 | Chitosan 10 cps (Biopolytec) | Polyacrylic acid Mw 450,000 (Aldrich) | 2.35:1 | 1.398 | 80.00% |
| PIC-21 | Chitosan 10 cps (Biopolytec) | Polyacrylic acid Mw 1,250,000 (Aldrich) | 2.35:1 | 1.206 | 52.30% |
| PIC-22 | Chitosan 10 cps (Biopolytec) | Polyacrylic acid Mw 3,000,000 (Aldrich) | 2.35:1 | 1.046 | 47.20% |
| PIC-23 | Chitosan 200 cps (Biopolytec) | Polyacrylic acid Mw 450,000 (Aldrich) | 2.35:1 | 1.29 | 92.90% |
| PIC-24 | Chitosan 200 cps (Biopolytec) | Polyacrylic acid Mw 1,250,000 (Aldrich) | 2.35:1 | 1.238 | 54.70% |
| PIC-25 | Chitosan 200 cps (Biopolytec) | Polyacrylic acid Mw 3,000,000 (Aldrich) | 2.35:1 | 1.367 | 48.30% |

As can be seen from the above table, the poly-ionic complex of the present disclosure showed good mucoadhesiveness. In addition, in case of PIC-15, all of 20 pieces were adhered for 24 hours it was confirmed that in ex vivo mucoadhesiveness test of Reference Example 4.

Comparative Examples 1 and 2: Preparation of a Mixture of Chitosan and Polyacrylic Acid 5 g of chitosan (Biopolytec, viscosity: 1000 cps, deacetylation degree: 82.2%) was dissolved in 2.5 L of distilled water with 10 ml of concentrated hydrochloric acid. 5 g of polyacrylic acid (Aldrich, molecular weight: 1,250,000) was dissolved in 5 L of distilled water. The two solutions were mixed and the pH was measured 1.8. Without adjusting the pH, the mixed solution was freeze dried to prepare a simple mixture. The obtained mixture was freeze milled to a size of 100 μm or less to obtain micronized powder of the simple mixture. A simple mixture was prepared with polyacrylic acid having molecular weight of 450,000 according to substantially the same process. Discs were formed according to the method of Reference Example 2, and in vitro mucoadhesiveness test was conducted according to the method of Reference Example 3. The results are shown below.

TABLE 3

| Sample | Chitosan | Polyacrylic acid | Ratio | Adhesion force (N) |
|---|---|---|---|---|
| Comparative Example 1 | Chitosan 1000 cps (Biopolytec) | Polyacrylic acid Mw 1,250,000 (Aldrich) | 2.35:1 | 0.849 |
| Comparative Example 2 | Chitosan 1000 cps (Biopolytec) | Polyacrylic acid Mw 450,000 (Aldrich) | 2.35:1 | 0.833 |

As can be seem from the above table, the simple mixtures of the Comparative Examples showed remarkably lower numerical values of mucoadhesiveness than the poly-ionic complex of the present invention.

Experimental Example 1: Residual Ratio in an Acidic Solution

The poly-ionic complex PIC-04 prepared in Example 1 and the simple mixtures of Comparative Examples 1 and 2 were tested according to the method disclosed in Reference Example 5 at pH 1.2 for 2 hours. The resulting residual ratios in an acidic solution as measured are as follows.

TABLE 4

| Sample | Residual ratio in an acidic solution (%) |
|---|---|
| Comparative Example 1 | 0.0 |
| Comparative Example 2 | 24.4 |
| Example PIC-08 | 97.4 |

As demonstrated from the above, the poly-ionic complex of the present disclosure showed very high residual ratio in an acidic solution.

Example 3: Preparation of Mucoadhesive Active Ingredient Particles 15.8 g of paliperidone, 47.4 g of Eudragit® RL PO (Evonik; the amount of chlorinated trimethylammonium methacrylate unit: about 10% by weight) and 236.8 g of Kollidon® SR were mixed well and fed into a twin screw extruder PET-015 (Vanho, Korea). The temperature was controlled in 3 divided zones, which was set properly for each zone within 70 to 140° C. (input zone: 70° C., mixing zone: 140° C., output zone: 125° C.; rotation speed: 100 rpm). The strands extruded from the die-head were made to have a uniform thickness of 800 μm (micrometer) by using a winder, and then, they were cut in a cylindrical form with a height of about 800 μm by using a cutter.

3.08 g of Eudragit® RS 100 (Evonik; the amount of chlorinated trimethylammonium methacrylate unit: about 5% by weight) was dissolved in a mixture solvent of 44 g of ethanol and 2.35 g of water, and 0.308 g of dibutyl sebacate and 1.5 g of talc were added thereto to prepare a polymer coating solution.

20 g of the pellet obtained above was mixed with 0.05 g of Aerosil, and fed as seed into mini-glatt (Glatt, Germany) equipped with microkit, and then coated by spraying the coating solution in bottom spray manner. After completing the spraying of the coating solution, the product was dried to obtain 22 g of a release control composition containing the drug.

The core (pellet) of the obtained composition was tested by the dissolution test in Reference Example 1, and it was confirmed that the drug was released slowly over 2 hours to 24 hours, and the dissolution pattern was close to zero order.

10 g of the pellet was put into mini-glatt fluidized bed coater and coated in bottom spray manner. The coating solution was prepared by dissolving 0.7 g of chitosan (Biopolytec, viscosity: 1000 cps, deacetylation degree: 82.2%) in 700 mL of distilled water with 1.4 ml of concentrated hydrochloric acid and dissolving 0.3 g of polyacrylic acid (Aldrich, molecular weight: 1,250,000) in 300 mL of distilled water, and then mixing the two solutions and dispersing 0.2 g of talc therein. The coating was conducted under the conditions of inlet air temperature of 32 to 40° C. and product temperature of 26 to 28° C. After completing the coating, the amount of the obtained drug-containing mucoadhesive pellet was 10.9 g. The specific coating conditions were as follows:

Process air: 0.25 to 0.40
Product temperature: 26 to 28° C.
Spray pressure: 0.60
Inlet temperature: adjusted between 32 and 40° C.

Example 4: Preparation of Poly-Ionic Complex-Containing Tablets

The micronized poly-ionic complex obtained in Examples 1 and 2 were mixed with the active ingredient and stearic acid according to the ratio in the following table, and tableting was conducted manually by utilizing a single station tablet press (EK-0, Korsch, Germany), to obtain tablets with weight of about 800 mg, long axis of 16.7 mm, short axis of 8.0 mm and thickness of 6 to 7 mm.

TABLE 5

| Sample | Poly-ionic complex | | Active ingredient | | Stearic acid | Total |
|---|---|---|---|---|---|---|
| T-1 | PIC-08 | 4.698 g | Paliperidone | 0.054 g | 0.048 g | 4.8 g |
| T-2 | PIC-15 | 4.698 g | Paliperidone | 0.054 g | 0.048 g | 4.8 g |
| T-3 | PIC-19 | 4.698 g | Paliperidone | 0.054 g | 0.048 g | 4.8 g |
| T-4 | PIC-19 | 4.75 g | Tamsulosin | 0.001 g | 0.048 g | 4.8 g |

Comparative Examples 3 and 4: Preparation of Lactose Tablets

For comparison, lactose, which are widely used in conventional tablets, was mixed with the active ingredient and stearic acid according to the ratio in the following table, and tableting was conducted manually by utilizing a single station tablet press (EK-0, Korsch, Germany), to obtain tablets with weight of about 800 mg, long axis of 16.7 mm, short axis of 8.0 mm and thickness of 6 to 7 mm.

TABLE 6

| Sample | Lactose | Active ingredient | | Stearic acid | Total |
|---|---|---|---|---|---|
| Comparative Example 3 (L-1) | 4.698 g | Paliperidone | 0.054 g | 0.048 g | 4.8 g |
| Comparative Example 4 (L-1) | 4.75 g | Tamsulosin | 0.001 g | 0.048 g | 4.8 g |

Example 5: Preparation of Tablets Containing a Mixture of a Poly-Ionic Complex and a Water Soluble Polymer The micronized poly-ionic complex obtained in Examples 1 and 2 were mixed with a water soluble polymer, polyethylene oxide (PEO) or hydroxypropyl methylcellulose (HPMC), the active ingredient and stearic acid according to the ratio in the following table, and tableting was conducted manually by utilizing a single station tablet press (EK-0, Korsch, Germany), to obtain tablets with weight of about 800 mg, long axis of 16.7 mm, short axis of 8.0 mm and thickness of 6.5 mm.

TABLE 7

| Sample | Poly-ionic complex | | Water soluble polymer | | Active ingredient | | Stearic acid | Total |
|---|---|---|---|---|---|---|---|---|
| T-5 | PIC-15 | 3.31 g | PEO | 1.44 g | Paliperidone | 0.054 g | 0.048 g | 4.8 g |
| T-6 | PIC-15 | 3.31 g | HPMC | 1.44 g | Paliperidone | 0.054 g | 0.048 g | 4.8 g |
| T-7 | PIC-19 | 3.31 g | PEO | 1.44 g | Paliperidone | 0.054 g | 0.048 g | 4.8 g |
| T-8 | PIC-19 | 3.31 g | HPMC | 1.44 g | Tamsulosin | 0.001 g | 0.048 g | 4.8 g |

Example 6: Preparation of Tablets Containing Mucoadhesive Active Ingredient Particles The micronized poly-ionic complex obtained in Examples 1 and 2 were mixed with a water soluble polymer, polyethylene oxide (PEO) or hydroxypropyl methylcellulose (HPMC), the mucoadhesive active ingredient obtained in Example 3 and stearic acid according to the ratio in the following table, and tableting was conducted manually by utilizing a single station tablet press (EK-0, Korsch, Germany), to obtain tablets with weight of about 800 mg, long axis of 16.7 mm, short axis of 8.0 mm and thickness of 6.5 mm.

TABLE 8

| Sample | Poly-ionic complex | | Water soluble polymer | | Mucoadhesive active ingredient particle | Stearic acid | Total |
|---|---|---|---|---|---|---|---|
| T-9 | PIC 15 | 3.54 g | — | — | 1.20 g | 0.048 g | 4.8 g |
| T-10 | PIC 15 | 2.48 g | HPMC | 1.06 g | 1.20 g | 0.048 g | 4.8 g |
| T-11 | PIC 19 | 2.48 g | PEO | 1.06 g | 1.20 g | 0.048 g | 4.8 g |
| T-12 | PIC 19 | 2.48 g | HPMC | 1.06 g | 1.20 g | 0.048 g | 4.8 g |

Experimental Example 2: Dissolution Test

Figure 1:
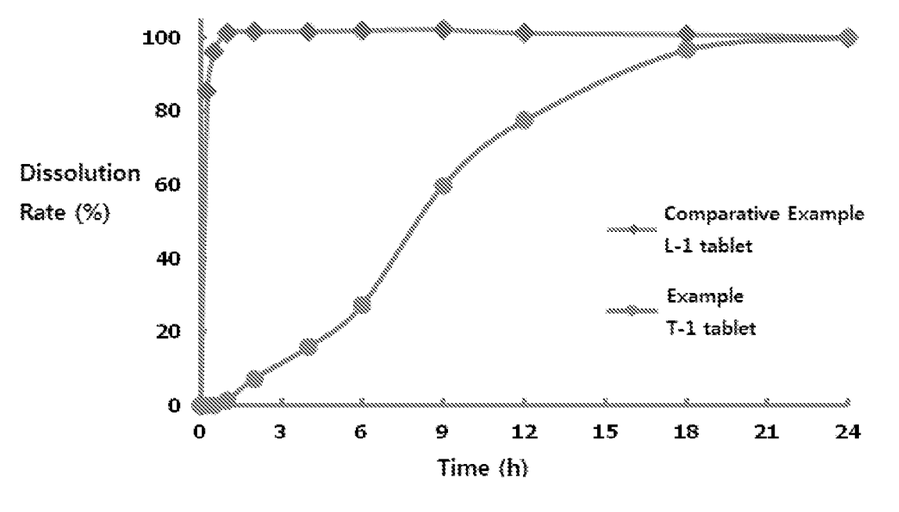
FIG. 1 is a graph showing comparative dissolution test results of the lactose tablet of the Comparative Example (L-1) and the poly-ionic complex-containing tablet of the present disclosure (T-1).

For the poly-ionic complex tablets (T-1) in Table 5 and the lactose tablets (L-1) of Comparative Example 3 in Table 6, the dissolution test was conducted according to the method in Reference Example 1, and the results are shown in FIG. 1. As shown in FIG. 1, the formulation of the present disclosure released the active ingredient over a long time nearly in zero order.

The invention claimed is:

1. A method for preparing a mucoadhesive pharmaceutical composition, comprising:
   (a) mixing an acidic aqueous solution of chitosan and an aqueous solution of polyacrylic acid, and then adjusting pH of a mixture to 5.0 to 6.0, to obtain a poly-ionic complex;
   (b) lyophilizing and milling the obtained poly-ionic complex of chitosan and polyacrylic acid to obtain a lyophilized and micronized poly-ionic complex; and
   (c) mixing the lyophilized and micronized poly-ionic complex with a water soluble polymer,
   wherein the water soluble polymer selected from the group consisting of water soluble cellulose ether, gelatin, alginate, dextrin, water soluble polyvinyl alcohol derivative and combinations thereof; and
   wherein a viscosity of the chitosan is 500 cps to 10,000 cps when measured for chitosan solution with 0.5% concentration in 1% acetic acid solvent at 25° C.; a molecular weight of the polyacrylic acid is 1,000,000 to 2,000,000; and a weight ratio of the chitosan to the polyacrylic acid is 1:0.3 to 1:1.

2. The method for preparing a mucoadhesive pharmaceutical composition according to claim 1, wherein the poly-ionic complex is micronized to have an average diameter of 1 nm to 300 μm.

3. The method for preparing a mucoadhesive pharmaceutical composition according to claim 1, further comprising mixing the lyophilized and micronized poly-ionic complex with an active ingredient.

4. The method for preparing a mucoadhesive pharmaceutical composition according to claim 3, wherein the active ingredient is in the form of micronized powder, crystalline solid, granule, particle or pellet.

5. The method for preparing a mucoadhesive pharmaceutical composition according to claim 3, wherein the active ingredient is one coated with a mixture of chitosan and polyacrylic acid.

* * * * *